United States Patent
Choudary et al.

(10) Patent No.: US 6,927,305 B2
(45) Date of Patent: Aug. 9, 2005

(54) PROCESS FOR PRODUCTION OF ALKANESULFONIC ACID

(75) Inventors: Boyapati Manoranjan Choudary, Hyderabad (IN); Kottapalli Koteswara Rao, Hyderabad (IN); Mahendar Koosam, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/393,403

(22) Filed: Mar. 20, 2003

(65) Prior Publication Data

US 2004/0186316 A1 Sep. 23, 2004

(51) Int. Cl.$^7$ ............................................. C07C 303/16
(52) U.S. Cl. ......................... 562/118; 562/30; 562/115
(58) Field of Search ............................ 562/118, 30, 115

(56) References Cited

U.S. PATENT DOCUMENTS

| 3,509,206 | A | * | 4/1970 | Nielsen | 562/6 |
| 4,239,696 | A | * | 12/1980 | Schreyer et al. | 562/118 |
| 4,808,341 | A | * | 2/1989 | Desgranchamps | 562/118 |
| 5,912,385 | A | * | 6/1999 | Kushibe et al. | 562/118 |

* cited by examiner

*Primary Examiner*—Rosalynd Keys
(74) *Attorney, Agent, or Firm*—Ladas and Parry LLP

(57) ABSTRACT

The present invention relates to a process for the production of alkanesulfonic acid. More particularly, the present invention relates to a process for the production of alkanesulfonic acid from alkyl mercaptan effluents generated in chemical industries. The process of the invention comprises the oxidation of the entire alkyl mercaptan generated as an effluent in the chemical industries to serve two concomitant purposes: (1) complete removal of obnoxious odor, and (2) value addition by the production of alkanesulfonic acids selectively in quantitative yields.

13 Claims, No Drawings

PROCESS FOR PRODUCTION OF ALKANESULFONIC ACID

FIELD OF THE INVENTION

The present invention relates to a process for the production of alkanesulfonic acid. More particularly, the present invention relates to a process for the production of alkanesulfonic acid from alkyl mercaptan effluents generated in chemical industries. The process of the invention comprises the oxidation of the entire alkyl mercaptan generated as an effluent in the chemical industries to serve two concomitant purposes: (1) complete removal of obnoxious odour, and (2) value addition by the production of alkanesulfonic acids selectively in quantitative yields.

More particularly, the present invention relates to in-situ production of value added methanesulfonic acid from methyl mercaptan generated as an effluent gas in pharmaceutical and pesticide industries such as in ranitidine and carbendazim production and also to eliminate air pollution.

BACKGROUND OF THE INVENTION

Emissions of mercaptan if not properly treated at the manufacturing site spreads into a blanket foul smell in ambient air and poses health hazards. Mercaptan is a heavy gas, wich once released, floats in the air and does not disperse easily with the smell lingering for hours. When inhaled, it is known to cause nausea, headache, irritation and vomiting, while prolonged exposure could be carcinogenic, affecting the lungs. Accordingly, it is of public concern that mercaptan be totally decomposed or converted into value added products to make the environment clean.

Sulfur compounds such as mercaptans, hydrogen sulfide etc are generated as effluents in a variety of industries, for example, in the paper, petroleum and gas refining, pharmaceutical, pesticide, and rubber manufacturing industries. The solutions adopted presently by the industry to control the emissions of the obnoxious gases like mercaptans are i) incineration of the pollutant gases (thermal combustion at higher temperatures or catalytic combustion), which has the draw back of producing again sulfur oxides that need scrubbing and also the cost of combustion is very high ii) adsorption of these gases on a solid phase like active charcoal, which has the draw back of vigorous heating-up and fire risks and also unable to recycle the charcoal iii) washing of the pollutant gases either with amines, sodium hydroxide or chlorine in the form of sodium hypochlorite or sodium chlorite solutions, which has the draw back of consumption of large amounts chemicals, make the treatment quite expensive. The chlorine and sodium hydroxide consumptions are high (8.5 and 7.6 mole/mole of methyl mercaptan removal respectively) iv) biodeoderization is achieved either by biomicroorganisms or by biofiltration which has the draw back of metabolization of coproducts and also requires installation of complex maintaining system. All of these solutions mentioned here have not only one or other drawbacks but also there is no recovery of any value added product obtained from the effluents.

Methanesulfonic acid is a high value product used as solvent, surfactant, catalyst in polymerization, alkylation and esterification reactions and also in electroplating industry. No method has been reported so far to our knowledge to obtain value-added product like methanesulfonic acid in-situ from an effluent gas methyl mercaptan generated during the chemical process in industries.

Some well-known methods of reactions of methyl mercaptan to produce methanesulfonic acid are mentioned herewith. For example, chlorination of methyl mercaptan produces methylsulfonyl chloride or methyl sulfonic acid that has the disadvantage of using corrosive chlorine gas as well as generation of large amounts of corrosive hydrogen chloride gas as byproduct that requires treatment. It is also known that mercaptans react with hydrogen peroxide in an alkaline medium to produce methanesulfonic acid via intermediate dialkyl disulfide. However, the peroxide to pollutant ratio of 5:1 is required to control odors as well as to get corresponding sulfonic acids. Here large excess of hydrogen peroxide is being used than stoichiometric quantities.

Reference is made to U.S. Pat. No. 5,605,635 (Feb. 25, 1997) wherein a process for purifying gaseous or liquid effluents containing sulfur-containing derivatives by basification of the effluent to be treated at pH>9 was described. Reference is also made to U.S. Pat. No. 4,729,835 (Mar. 8, 1988) wherein a process for waste treatment of dimethyl disulphide was disclosed using hydrogen peroxide at a pH 8.5 to 11.5 in the presence of tungstate catalyst. The drawbacks in the above processes are that there is no mention of recovering of any value-added product except to control the emission of the foul smelled gases.

Reference is further made to U.S. Pat. No. 4,239,696 (Dec. 16, 1980) wherein alkylsulfonic acids are prepared by oxidation of alkyl mercaptan or dialkyl disulfide with hydrogen peroxide. This is a synthetic method of preparation of alkylsulfonic acids and this work was not directed for the elimination of the obnoxious gases of effluent streams generated at chemical industries.

OBJECTS OF THE INVENTION

The main object of the invention is to provide a process for the oxidation of entire alkyl mercaptan generated as effluent in chemical industries to serve two purposes concomitantly (1) complete removal of obnoxious odour, and (2) value addition by the development of a process for the manufacture of alkanesulfonic acid selectively in quantitative yields which obviates the drawbacks detailed above.

It is another object of the invention to provide a process for the conversion of alkyl mercaptans to alkanesulfonic acids which is environmentally friendly and eliminates obnoxious gases completely.

A further object of the invention is to provide a process for the conversion of alkyl mercaptans generated as effluents in chemical industries to alkane sulfonic acids by a simple methodology which is easily implementable at the industrial site, is economical and results in value added products.

Another object of the present invention is complete elimination of obnoxious gases generated as gaseous effluent from pharmaceutical and pesticide industries such as in the synthesis ranitidine and carbendazim.

SUMMARY OF THE INVENTION

Accordingly, the present invention provides a process for the production of an alkanesulfonic acid comprising reacting the corresponding alkyl mercaptan and aqueous hydrogen peroxide using the same alkanesulfonic acid generated as a catalyst.

In one embodiment of the invention, the alkyl mercaptan is selected from the group consisting of methyl, ethyl, propyl and butyl mercaptan.

In another embodiment of the invention, the alkyl mercaptan used is obtained as the effluent gas from chemical and pharmaceutical industries.

In a further embodiment of the invention, the alkyl mercaptan used is methyl mercaptan generated as gaseous effluent during the synthesis of ranitidine and carbendazim.

In another embodiment of the invention methyl mercaptan gas generated in situ in the synthesis of ranitidine drug is reacted with aqueous hydrogen peroxide to obtain methanesulfonic acid.

In another embodiment of the invention methyl mercaptan gas generated in situ in the synthesis of carbendazim pesticide is reacted with hydrogen peroxide to obtain methanesulfonic acid.

In another embodiment of the invention alkyl mercaptan is totally converted to the corresponding alkanesulfonic acid.

In another embodiment of the invention the concentration of hydrogen peroxide used is in the range of 5–50%.

In still another embodiment of the present invention alkanesulfonic acid employed as catalyst is in the range of 1 to 10 mol % with respect to alkyl mercaptan.

In another embodiment of the invention the oxidation reaction takes place at a temperature in the range of 25–70° C.

In another embodiment of the invention, the reaction time is in the range of 4–15 hrs.

In a further embodiment of the invention, water is obtained as a byproduct.

DETAILED DESCRIPTION OF THE INVENTION

The novelty of the present invention lies in the oxidation of the alky mercaptan generated as an effluent in the chemical industries in presence of a catalyst which fulfills twin objectives: effective removal of the obnoxious gases completely and production of a value added product, alkanesulfonic acids selectively in quantitative yields by use of alkyl mercaptan. Expenditure is incurred presently for removal of these obnoxious gases by the industry using various methods; however the present process has the advantage of earnings by selling the product thus obtained. The set up for this reaction is very simple and easily adaptable at the site of the industries that produce these mercaptan gases. The process described herein uses mild operating conditions and no further effluent is generated from this reaction. Thus this invention offers the best route not only for the complete removal of obnoxious gases but also for the production of value added alkanesulfonic acids.

The process of the present invention utilises alkyl mercaptans generated as effluent gas in chemical and pharmaceutical industries. The process of the invention comprises the oxidation of the entire alkyl mercaptan generated as an effluent in the chemical industries to serve two purposes concomitantly: (1) complete removal of obnoxious odour, and (2) value addition by the production of alkanesulfonic acids selectively in quantitative yields, comprising the reaction of the alky mercaptan (alkyl=methyl, ethyl, propyl and butyl) and aqueous hydrogen peroxide at 25–70° C. for 4–15 hours using the same alkanesulfonic acid to be produced as the catalyst thereby overcoming requirements of catalyst separation and contamination.

The process of the invention is useful, for example in the in-situ production of value added methanesulfonic acid from methyl mercaptan which is generated as an effluent gas in the pharmaceutical and pesticide industries such as in ranitidine and carbendazim production and also to eliminate air pollution.

The concentration of hydrogen peroxide used is in the range of 5–50%. The alkanesulfonic acid employed as catalyst is in the range of 1 to 10 mol % with respect to methyl mercaptan generated. Water is obtained as a byproduct.

The invention is further explained by reference to Scheme 1, which illustrates the present reaction scheme in the production of methanesulfonic acid.

Scientific Explanation:

The use of hydrogen peroxide mediated oxidations is considered ecofriendly, since it leaves water as a byproduct. Further the oxygen content is very high when compared to other oxidants and next to molecular oxygen. The handling of hydrogen peroxide is safer than molecular oxygen in the oxidation reactions. The present oxidation of alkyl mercaptan to alkylsulfonic acid is induced by Bronsted acid and in situ generated peracid. No separate initiator is required The present invention is aimed at not only for the complete removal of obnoxious gases but also for the production of value added alkanesulfonic acids.

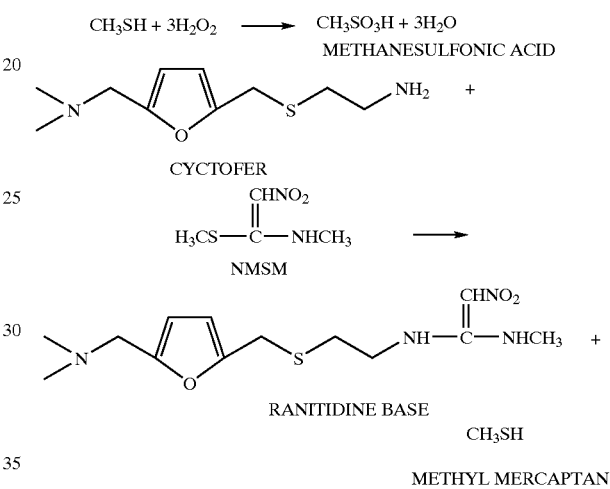

Scheme 1

The following examples are given by way of illustration and therefore should not be construed to limit the scope of the present invention.

EXAMPLE 1

The reaction set up consists of two parts; one for the generation of methyl mercaptan gas as practiced at industry in the manufacture of ranitidine base and the second one for the oxidation reaction of the methyl mercaptan gas thus generated in-situ. (Scheme 1)

First part of the reaction is as follows: Reaction is conducted in a 25 L round-bottomed 4-necked glass vessel to which a mechanical Stirrer, a thermometer socket, a pressure equalising funnel and an outlet tube are provided. This vessel is placed in a metallic tub having the provisions for heating and cooling system so that it provides the necessary temperature for the reaction. NMSM (99%) 3.5 Kg (23.65 mol) and water 8L were taken into the vessel, mixed well with the mechanical stirrer and raised the temperature to 40° C. Then cystofer (95.5%) 5.3 Kg (23.65 mol) was added continuously over a period of 4 hrs while maintaining the temperature of the reaction at 40° C. Reaction was continued further 6 hrs for completion. Methyl mercaptan gas started generating upon the addition of cystofer and continues to generate till the end of the reaction (10 hrs).

The second part of the reaction is as follows: Methyl mercaptan gas thus generated in the first part of the reaction was passed from the outlet tube simultaneously to a 4-necked 25 L round bottomed glass vessel (similar set up as described in the first part of the reaction) through a dip tube containing 8.5 L of hydrogen peroxide (14%) (35 mol) and 0.125 Kg of methanesulfonic acid as catalyst. While the stirrer was put on continuously, temperature of this reaction was also maintained at 40° C. (+ or–5° C.) by manouevering heating and cooling continuously through out the reaction. Additional quantity of 4L of hydrogen peroxide (30%) (35 mol) was added continuously after one hour of the mercaptan gas generation for over a period of 3.0 hrs. The reaction was maintained at 40° C. for another 6.0 hrs. At the end of the reaction this flask was heated to 100 to 110° C. to decompose any hydrogen peroxide that is not reacted completely. Distillation is carried out under reduced pressure and the methanesulfonic acid was obtained in quantitative yields (1.93 Kg) accounting to the total amount of mercaptan charged into the second reactor from the first reactor.

The Main Advantages of the Present Invention are:
1. The selectivity and yields of alkanesulfonic acids are quantitative.
2. The present process is environmentally friendly and eliminates obnoxious gases completely.
3. Implementation of this process at the industrial site is very simple.
4. Value added products are obtained.

We claim:
1. A process for the production of an alkanesulfonic acid comprising reacting in situ the corresponding alkyl mercaptan that is generated as an effluent gas in a chemical process and aqueous hydrogen peroxide in the presence of alkanesulfonic acid as a catalyst wherein the alkanesulfonic acid is in the range of 1 to 10 mol % with respect to the alkyl mercaptan.

2. The process as claimed in claim 1 wherein the alkyl is selected from the group consisting of methyl, ethyl, propyl and butyl.

3. The process as claimed in claim 1 wherein the alkyl mercaptan used is methyl mercaptan.

4. The process as claimed in claim 3 wherein the methyl mercaptan is reacted with aqueous hydrogen peroxide to obtain methanesulfonic acid.

5. The process as claimed in claim 1 wherein all the alkyl mercaptan is converted to the corresponding alkanesulfonic acid.

6. The process as claimed in claim 1 wherein the concentration of hydrogen peroxide in the aqueous solution is in the range of 5–50 mol %.

7. The process as claimed in claim 1 wherein the reaction takes place at a temperature in the range of 25–70° C.

8. The process as claimed in claim 1 wherein the reaction time is in the range of 4–15 hrs.

9. The process according to claim 1 wherein the chemical process is an industrial process.

10. The process according to claim 1 wherein the chemical process is a process for producing a product used in the preparation of a pharmaceutical product.

11. The process according to claim 1 wherein the chemical process is a process for producing a product used in the preparation of a pesticide.

12. The process according to claim 1 wherein the chemical process is a process for producing ranitidine.

13. The process according to claim 1 wherein the chemical process is a process for producing carbendazim.

* * * * *